United States Patent [19]

Tabak et al.

[11] 4,211,886

[45] * Jul. 8, 1980

[54] MANUFACTURE OF BENZENE, TOLUENE AND XYLENE

[75] Inventors: Samuel A. Tabak, Wenonah; Roger A. Morrison, West Deptford, both of N.J.

[73] Assignee: Mobil Oil Corporation, New York, N.Y.

[ * ] Notice: The portion of the term of this patent subsequent to Feb. 12, 1997, has been disclaimed.

[21] Appl. No.: 945,279

[22] Filed: Sep. 25, 1978

[51] Int. Cl.$^2$ ............................. C07C 3/62; C07C 5/30
[52] U.S. Cl. .................................... 585/321; 585/474; 585/475; 585/481; 585/905
[58] Field of Search ............................ 208/66, 135, 64; 260/668 A, 672 T

[56] References Cited

U.S. PATENT DOCUMENTS

| | | | |
|---|---|---|---|
| 3,965,209 | 6/1976 | Butter et al. | 260/671 R |
| 4,039,599 | 8/1977 | Gewartowski | 260/668 A |
| 4,101,597 | 7/1978 | Breckenridge | 260/668 A |

Primary Examiner—Herbert Levine
Attorney, Agent, or Firm—Charles A. Huggett; Raymond W. Barclay

[57] ABSTRACT

Benzene, toluene and xylene are produced in high yield from aromatic naphtha by a processing technique which combines (1) high temperature isomerization of eight carbon atom aromatics over a catalyst having relatively low activity and constrained access to the internal pore surface and (2) processing of heavy single ring aromatics of nine or more carbon atoms together with toluene under dealkylation/transalkylation conditions. The effluents of the two reactions are blended for processing through separation and recovery equipment. The unique chemistry of the isomerization stage results in splitting off alkyl side chains of two or more carbon atoms while retaining methyl groups attached to aromatic rings. Because of these reaction characteristics, full range reformate is advantageously added to the isomerizer charge for conversion to methyl benzene and redistribution of methyl groups to the thermodynamic equilibrium values.

37 Claims, 1 Drawing Figure

MANUFACTURE OF BENZENE, TOLUENE AND XYLENE

FIELD OF THE INVENTION

The invention is concerned with improved techniques for manufacture of benzene, toluene and xylene (BTX) from commercially available light hydrocarbon fractions commonly called "naphtha". The preferred source material is constituted by a class of naphtha prepared by catalytic reforming of liquid petroleum fractions boiling below about 400° F. Reforming results in a reformate product of increased aromatic content due primarily to dehydrogenation of naphthenes under hydrogen pressure in the presence of a strong dehydrogenation catalyst such as platinum on a porous support at temperatures upwards of about 850° F. Other charge stocks which may be used include pyrolysis gasoline, coal tar naphthas and the like.

It is an important object of the present invention to recover BTX from the known charge materials with a minimum of pretreatment as by solvent extraction to separate aliphatic hydrocarbons and distillation to isolate the fractions rich in BTX. It is a further object to convert aromatic components other than BTX in such manner that all, or substantially all, aromatic rings in the charge are recovered as BTX product.

BACKGROUND OF THE INVENTION

The presence of the valuable chemical raw materials referred to as BTX in petroleum and other naphthas has long been recognized and many techniques have been described for recovery of these single ring aromatics from their admixture with aliphatic hydrocarbons of like boiling point. Early practice favored extraction with selective solvents to separate aromatics from aliphatics. The aromatic concentrate so derived is readily distilled to yield benzene and toluene at desired purity. The four $C_8$ aromatics ethylbenzene (EB) and the three xylene isomers pose a more difficult problem because their boiling points are within the narrow range of 277.1° F. for EB to 292° F. for o-xylene. The great differences in freezing point provide basis for separating $C_8$ components by fractional crystallization. Extensive facilities have been installed for recovery of p-xylene in this manner, after which the $C_8$ aromatics mixture lean in p-xylene can be subjected to catalytic isomerization to generate additional desired p-xylene from o- and m-xylene and the product enriched in p-xylene recycled to the fractional crystallization stage. This leaves EB unchanged to accumulate in the isomerizer/crystallizer "loop" unless steps are taken to remove it.

One approach to that problem of EB build-up was the Octafining process which isomerizes xylenes under hydrogen pressure in the presence of platinum on silica-alumina catalyst. Under Octafining conditions, EB is hydrogenated to ethylcyclohexane, isomerized to dimethylcyclohexane and dehydrogenated to xylene. Concurrent conversion of xylene to undesired by-products is such as to result in net loss of xylene despite the conversion of EB to xylene. That history of Octafining is set out in more detail by U.S. Pat. No. 3,856,872 which describes a major advance by conducting the isomerization in the presence of a catalyst in which the acidic component is a zeolite such as ZSM-5. The entire contents of said patent are incorporated herein by reference.

An improved method for preparing $C_8$ aromatic fractions from reformate and other sources is described in U.S. Pat. No. 3,945,913 and U.S. Pat. No. 4,078,990, the full contents of each being herein incorporated by this reference. According to that technique, heavy reformate or the like, containing hydrocarbons of at least nine carbon atoms is reacted in the presence of hydrogen under conditions to dealkylate aromatics and concurrently hydrocrack paraffins to lower boiling compounds to be later separated by distillation. This "heavy aromatic processing" yields a distillate $C_8$ fraction low in EB and free of paraffinic hydrocarbons. An advantageous combination of heavy aromatics processing with the vapor phase isomerization of U.S. Pat. No. 3,856,872 is described in patent application Ser. No. 809,231 filed June 23, 1977 now U.S. Pat. No. 4,101,597, the entire contents of which are incorporated herein by this reference. By the process of that application, heavy ($C_9+$) aromatics generated in vapor phase isomerization are converted over a suitable catalyst, preferably in admixture with toluene. Effluents of heavy aromatics processing and of the isomerizer are blended for flash separation of recycle hydrogen and processed together through the product recovery steps.

A still further improvement in xylene manufacture is set out in our prior application Ser. No. 914,645, filed June 12, 1978, the entire contents of which are incorporated herein by this reference. Using as catalyst a combination of metal and a zeolite having very low activity and constrained access to the inner pore area of the zeolite (such as ZSM-5), isomerization of xylenes is achieved at very low xylene loss. During conversion there is a small amount of disproportionation, generally less than 1% of the xylene to toluene and trimethylbenzene. Alkyl chains of two or more carbon atoms are split off, thus eliminating ethylbenzene from the stream in the loop. Because the catalytic isomerizer lacks disproportionation activity, such compounds as trimethylbenzene would build up in the loop unless a $C_9'$ fraction were withdrawn. However, because the conversion removes side chains of two or more carbon atoms, it can accept the heavy end of a reformate to make benzene from ethylbenzene, toluene from methylethylbenzene, xylene from dimethylethylbenzene and the like.

SUMMARY OF THE INVENTION

Process flow is simplified by elimination of separation steps and overall efficiency in manufacture of BTX from reformate and the like by combining our high temperature isomerization process with heavy aromatics processing in a particular manner. Specifically, reformate, preferably the full effluent of a catalytic reformer, is charged to high temperature isomerization. The isomerizate is fractionated and the cut boiling above $C_8$ is charged, preferably in admixture with toluene, to heavy aromatic processing.

BRIEF DESCRIPTION OF THE DRAWINGS

A preferred embodiment of the invention is illustrated in the single figure of the annexed drawings which provide a diagrammatic flow-sheet of that embodiment.

DESCRIPTION OF SPECIFIC EMBODIMENTS

The specific combination of high temperature isomerization over low activity, constrained access zeolite with heavy aromatic processing provides unusual benefits. The high temperature isomerization process will accept the full reformate or a desired fraction thereof and will produce therefrom a product stream consisting essentially of the low boiling paraffins benzene and methyl benzenes including toluene, xylenes, trimethylbenzenes and higher boiling methyl benzenes. Distillation of that stream separates low boiling paraffins suited for use as fuel gas, benzene, toluene, a $C_8$ fraction for recovery of desired xylene isomer and a heavy $C_9+$ fraction of heavy aromatics. The latter fraction is essentially trimethyl benzene and heavier methyl benzenes which cannot be recycled to advantage to the isomerizer. One prominent advantage of this style of isomerization is the lack of disproportionation activity, thereby inhibiting loss of xylene by that route. However, that property of the catalyst renders it incapable of converting trimethyl and higher methylbenzenes to xylenes. According to the present invention, these are now transferred to heavy aromatic processing where they are transalkylated with toluene and/or disproportionated to generate additional BTX, particularly benzene and xylene. The efficiency of the heavy aromatics processing is also enhanced in this combination because the aromatic side chains of more than one carbon atom are split off in high temperature isomerization and do not survive the separation steps to disturb operation of the heavy aromatics processing. Because of these characteristics, the two catalytic reactors complement each other in such manner that hydrocarbons supplied to the combination may be recycled to extinction in the usual case. The invention contemplates withdrawal of a drag stream of heavy material if needed to keep the system in balance, but for the most part, fuel gas and desired BTX products constitute the effluent streams.

The characteristics of the isomerizer employed in the invention, as complemented by the heavy aromatics processing, are such that conventional separation steps in preparing charge stock for aromatics manufacture from reformate can be eliminated. The solvent extraction step conventional in this art becomes unnecessary because paraffins are hydrocracked in the isomerizer to low boiling hydrocarbons easily removed by the distillation required in a recovery loop. Ability of the combination to handle heavy aromatics, alternatively in the isomerizer or the or the heavy aromatics processing, and product BTX makes it possible to charge the full reformate. Hydrogen is required in the isomerizer. It is feasible to derive that component as all or part of the hydrogen present in the reformer effluent. This eliminates or reduces service of the high pressure separator normally associated with reformers. In a preferred embodiment, the entire reformer effluent is "cascaded" to the isomerizer in that fashion to omit the conventional train of high pressure separator, distillation to isolate the $C_8$ fraction and extraction by solvents to remore paraffins. This embodiment not only omits expensive capital equipment but also saves the utilities costs associated with cooling and reheating and with depressuring and recompression.

A convenient expedient for cascade processing is to use the final reactor of the reformer train as the isomerization vessel. It will be recognized that, depending on overall economics, a partial release of hydrogen in a high pressure separator after the reformer may be utilized to adjust the quantity of hydrogen supplied to the isomerization stage. Thus the invention not only couples isomerization at high temperature with heavy aromatics processing, but also, in its preferred embodiment, couples those two processes with reforming in a single process train.

The catalyst in the heavy aromatics reactor may be any acidic porous solid catalyst having pores of a size to admit the reactants, say a constraint index as hereinafter defined of less than about 12.

The isomerization catalyst and the preferred catalyst for heavy aromatic processing are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain a degree of crystallinity for long periods in spite of the presence of steam at high temperature which induces irreversible collapse of the framework of other zeolites, e.g. of the X and A type. Furthermore, carbonaceous deposits when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination a silica to alumina mole ratio of at least about 12; and a structure providing constrained access to the crystalline free space.

The zeolite will have a silica/alumina ratio greater than 12. In a preferred embodiment, the desired low activity of the isomerization catalyst is achieved by unusually high silica/alumina ratio, greater than 200, preferably above about 500.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acqure an intracrystalline sorption capacity for normal hexane which is greater than that for water, i.e. they exhibit "hydrophobic" properties. It is believed that this hydrophobic character is advantageous in the present invention.

The type zeolites described freely sorb normal hexane and have a pore dimension greater than about 2 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methyl pentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperatures employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraing index, as utilized herein, while affording a highly useful means for characterizing the zeolites of interest is approximate, taking into consideration the manner of its determination, with probability, in some instances, of compounding variables extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by refernce.

ZSM-38 is more particularly described in U.S. Pat. No. 4,046,859, the entire contents of which are incorporated herein by reference.

A particularly preferred form of zeolite ZSM-5 is formed by crystallization of the zeolite from a solution containing metal ions, such as platinum as described in application Ser. No. 813,406 filed July 5, 1977 now abandoned, the entire contents of which are incorporated herein by reference.

The best results so far have been obtained with such ZSM-5 variants prepared by co-crystallization of metal and zeolite which are conveniently given the designation ZSM-5- (cc M), where M stands for the metal co-crystallized (cc) with the zeolite during synthesis. ZSM-5-(cc Pt) with 0.2–0.8 wt % Pt has proved particularly effective in the present process.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-35, and ZSM-38, with ZSM-5 or its metal containing variant particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pykometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such an alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The isomerizer utilizes zeolites of the type described, limited however to those forms which are of relatively low acid activity. It has been found that, as activity of these zeolites is reduced, the capacity to catalyze disproportionation declines without substantial decline in the capacity to catalyze isomerization of xylenes at temperatures above 800° F. The invention takes advantage of that unique characteristic to achieve the processing advantage that isomerization is decoupled from ethylbenzene conversion which now proceeds by dealkylation in the presence of the low activity zeolite and the metal component. A significant consequence of these catalytic properties is that recycle of toluene and trimethylbenzene to the isomerization reactor is generally undesirable. The lack of disproportionation activity means that these methylbenzenes will not be converted in significant amounts to xylenes. Hence these species which are unreactive in the isomerizer are recycled only to heavy aromatics processing to avoid build-up in the loop of diluent materials.

Figure 1:
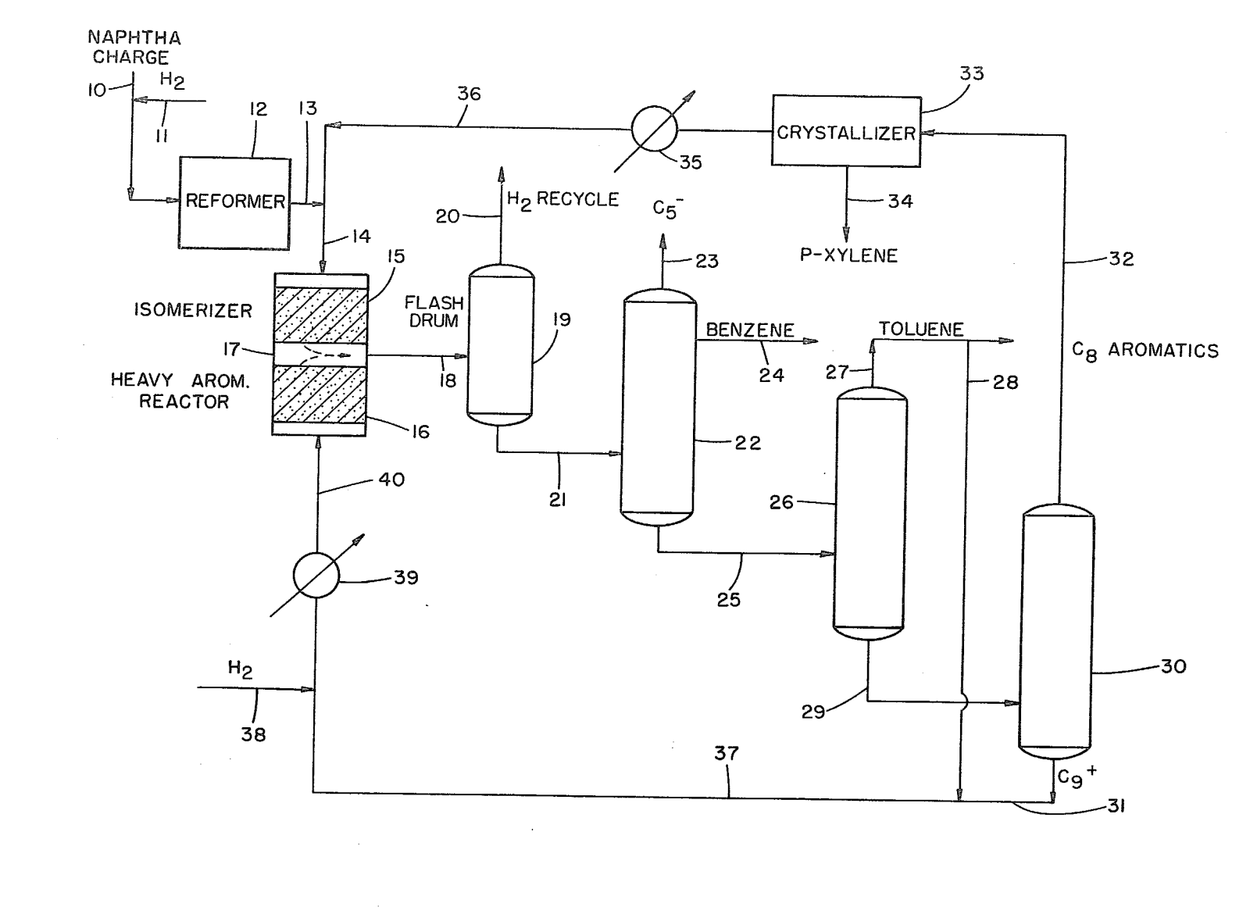

Referring now to the flow sheet set out in the drawing, a preferred form of the invention involves charge of the entire effluent of a catalytic reformer to the isomerization/product recovery loop. A suitable naphtha such as the $C_6$–380° F. cut from a crude petroleum is supplied at charge line 10, admixed with hydrogen from line 11 and introduced to a catalytic reformer 12. The mixture of hydrogen and naphtha is contacted in reformer 12 with catalyst such as platinum on alumina at temperatures upwards of 850° F. and pressures between about 200 and 600 psi. Among the complex of reactions taking place in the reformer, dehydrogenation of naphthenes is of primary importance, forming benzenes from cyclohexane and alkylated benzenes from alkyl cyclohexanes. Because of the cut point of the naphtha charge, no fused ring compounds (e.g. naphthalene) are found in the reformate product.

In conventional practice the reformate, now enriched in single ring aromatics by catalytic reactions in the reformer, is subjected to low pressure flash distillation to separate hydrogen for recycle in the process, fractionated to separated a $C_8-$ cut and the latter is solvent extracted to obtain a fraction consisting essentially of aromatic compounds of 6 to 8 carbon atoms from which desired compounds are recovered. The invention contemplates optional operations in which one or more of these separation steps are conducted on the reformate. In the preferred embodiment of the drawing, the full effluent of the reformer, hydrogen and all, is cascaded to an isomerization/recovery loop by line 13.

The loop has many conventional features in recovery of p-xylene from an aromatic stream, isomerization of the $C_8$ aromatics lean in p-xylene and recycle of the isomerate to the p-xylene recovery step after removal of compounds boiling above and below $C_8$ aromatics. The loop departs from convention in conducting the isomerization in accordance with our said application Ser. No. 914,645 and in adding the reformate to the isomerizer charge.

Reformer effluent from line 13 is mixed with a $C_8$ fraction lean in p-xylene from a xylene recovery step presently to be described. The combined hydrocarbon stream is passed by line 14 to an isomerization reactor 15. If the reformate has been flashed to separate hydrogen, it will be necessary to add hydrogen to the isomerizer charge. In the embodiment shown, hydrogen is part of the reformer effluent. As noted above, the bed of isomerization catalyst may be in the final reactor of the reformer reactor train. The catalyst in isomerizer 15 is a crystalline aluminosilicate zeolite having a constraint index of 1 to 12, which zeolite is of substantially reduced activity. Preferably, the zeolite is associated with a metal having hydrogenation/dehydrogenation activity, such as a metal from Group VIII of the Periodic Table, preferably a noble metal such as platinum or palladium. The temperature is maintained in the range of 800° F. to 1000° F.

Reduced activity of the zeolite for the present purpose may be attained by high silica/alumina ratio (above about 200), by dilution with a high preponderance of inert matrix, severe steaming, partial coking and other techniques known in the art.

The catalyst in isomerizer 15 promotes a reaction course which is unique at temperatures upwards of 800° F. Ethylbenzene in the charge is selectively cracked to benzene and ethane at little or no conversion of xylenes. Two or more carbon atom chains on other aromatics undergo like conversion. The two types of conversion are decoupled such that reaction severity is not a compromise to achieve effective ethyl aromatic conversion at "acceptable" loss of xylene. This characteristic of the process renders unnecessary the preliminary distillation to separate at least some of the ethyl benzene and $C_9+$ aromatics from the feed stream as practiced in prior processes. It has been further found that the present process has capability to convert paraffin hydrocarbons. This makes it possible to dispense with the expensive extraction step conventionally applied to a fraction of catalytically reformed naphthas in the manufacture and recovery of xylenes. In taking advantage of this feature, the feed stream at line 13 will contain the $C_6+$ aromatics of a reformate or the like together with the paraffins of like boiling range, hexanes and heavier. The paraffins in the charge are hydrocracked to lighter paraffins which will come off in the distillation train presently to be described in much greater quantity than that resulting from conversion of ethylbenzene.

The ability of the process to handle heavy aromatics presents the possibility of charging to the reformer a wider cut than the 310° F. end point naphtha commonly employed, resulting in heavier aromatics in charge to the reactor of this process. Those heavy aromatics will be converted to provide additional benzene and toluene plus additional trimethyl benzene valuable as a source of additional BTX as will appear below.

The low acid activity of the catalyst is attainable in any of several ways or a combination of these. A preferred alternative is to form the zeolite at high silica/alumina ratio above 200, preferably above 500. Very high dilution with an inert matrix is also effective. For example, composites of a more active form of zeolite ZSM-5 with alumina at a ratio of 5 parts of zeolite with 95 parts of the inert matrix provides a suitable catalyst as described in our application Ser. No. 795,046, filed May 9, 1977 now abandoned, the entire contents of which are incorporated herein by reference.

Activity of these zeolites may be reduced to levels suited to practice of the invention by thermal treatment or steam at high temperature as described in application Ser. No. 582,025, filed May 22, 1975 now U.S. Pat. No. 4,016,218 and in U.S. Pat. No. 3,965,209, respectively. Zeolites employed in such severe reactions as aromatization of paraffins and olefins lose activity to an extent which makes them suitable for use in the process of this invention. See U.S. Pat. No. 3,960,978 for fuller discussion of this manner of deactivated zeolite. Another method for reducing activity is to provide basic cations such as sodium as a significant proportion of the cationic sites of the zeolite. That technique is described in U.S. Pat. No. 3,899,544.

By whatever means the reduced acid activity is achieved, the activity may be measured in terms of disproportionation activity. A suitable test for the purpose involves contacting xylenes in any convenient mixture or as a single pure isomer over the catalyst at 900° F., 200 psig and liquid hourly space velocity (LHSV) of 5. Suitable catalysts for use in the process of the invention will show a single pass loss of xylenes (by disproportionation) of less than 2 weight percent, preferably less than one percent. Catalysts which have been employed show losses in the neighborhood of 0.5 percent. It is this very low rate of disproportionation at very high levels of ethylbenzene conversion to benzene (about 30%) that provides the advantage of the new chemistry of aromatics processing characteristic of the invention. That lack of disproportionation (and transalkylation generally) activity also dictates separate treatment of compounds boiling above and below eight carbon atom aromatic compounds.

The product of isomerizer 15 is admixed with the effluent from a heavy aromatics reactor 16 (hereinafter described in more detail) in plenum chamber 17 and passed by line 18 to a flash drum 19 where hydrogen is separated at a reduced pressure and withdrawn by line 20 for recycle to reformer 12, heavy aromatics reactor 16 and to isomerizer 15 if the option is taken of separating hydrogen from the reformer effluent.

Bottoms from flash drum 19 are constituted by hydrocarbons which pass by line 21 to fractionating column 22. The overhead of column 22 in line 23 is made up of hydrocarbons boiling below benzene, essentially paraffins, which may be used for fuel gas or other purposes as is well known in the art. Benzene may be withdrawn as a sidestream at line 24, while column 22 bottoms pass by line 25 to toluene tower 26. Toluene overhead of tower 26 may be recovered as a product from line 27 or recycled in the process through line 28, preferably the latter. Tower 26 bottoms pass by line 29 to splitter 30 from which bottoms of $C_9+$ aromatics are recycled to heavy aromatics reactor 16 by line 31.

The overhead from splitter 30 is constituted by $C_8$ aromatics, primarily xylenes at the equilibrium value since ethylbenzene of the reformer effluent is converted in isomerizer 15 after the fashion described above. That overhead passes by line 32 to suitable equipment for recovery of desired xylene isomer or isomers, such as crystallizer 33 wherein the $C_8$ aromatics are chilled, and filtered to separate crystals of p-xylene from the isomers of lower freezing point. The p-xylene product is withdrawn at line 34 while the mixture lean in p-xylene is heated at heat exchanger 35 and recycled by line 36 to mix with reformer effluent from line 13 and be admitted through line 14 to isomerizer 15.

The $C_9+$ bottoms in line 31 are preferably blended with toluene from line 28 and the mixture passes by line 37 to be mixed with hydrogen from line 38, heated in heat exchanged 39 and passed by line 40 to heavy aromatics reactor 16.

Preferred catalysts for heavy aromatics processing are those zeolites having a constraint index of 1 to 12 and a silica/alumina ratio of at least 12, typified by zeolite ZSM-5. This operation proceeds well with any acidic, hetergeneous catalyst having pores suited to admission of the aromatic molecules to the inner sorption area of the catalyst including amorphous silica-alumina and other such catalysts having a constraint index less than unity. Thus, acidic catalysts having constraint indices below 12, including the crystalline zeolites and the amorphous catalysts are generally useable. Such heavy aromatics processing over zeolites of 1-12 constraint index is described in U.S. Pat. No. 3,945,913. The finding of general applicability of acid catalysts (except those zeolites having pores too small to admit aromatics) is reported and the more general process is described in U.S. Pat. No. 4,078,990.

As study proceeded with respect to the process of those patents, examination of the reaction kinetics provided an explanation of the unique chemistry involved. It is found that dealkylation of alkyl side chains having two or more carbon atoms is extremely rapid, proceeding to near completion in the shallow portion of the catalyst bed first contacted by the reactants. For that reason, the mixture brought into contact with the major portion of the catalyst is constituted by methyl benzene diluted by alkanes of two or more carbon atoms. The reaction occuring in that major portion of the bed is therefore transalkylation (including disproportionation) of methyl benzenes to approach the thermodynamic equilibrium. From these findings, it was reasoned that the reaction should proceed with any acid hetergeneous catalyst since these are known to have activity for hydrodealkylation and for transalkylation.

Upon testing that hypothesis, it was found that the unique course of the reaction does indeed take place with solid, porous catalyst having acid activity. U.S. Pat. No. 4,078,990 is directed to that extension of the novel process to include use of such acid catalysts other than the particular zeolites described in our said patent.

Typically, the catalysts of the latter invention differ from those of the prior patent in having pores of such size that hydrocarbon molecules of the sizes found in reformates freely pass therethrough at about the same rate of diffusion, a property defined as "constraint index" not greater than unity. The catalysts of this application thus include such crystalline aluminosilicate zeolites as X, Y, mordenite, beta, as well as the amorphous acid catalysts. The amorphous acid catalysts of greater present importance in commercial use are composites of silica and alumina prepared as co-gels, co-precipitates or milled mixtures of silica and alumina gels or precipitates. Alternatively, these mixtures may be prepared by precipitating one oxide on a gel or precipitate of the other. Other acid porous oxides are also contemplated such as silica-zirconia, silica-thoria, silica-magnesia and the like.

The most active form of catalyst for the present purpose are those in which cationic sites are occupied at least in part by protons, sometimes called the "acid form". Protons may be introduced by base exchange with ammonium or amine cations and calcination to decompose the ammonium or substituted ammonium cation.

Preferably, the catalyst also includes a metal having hydrogenation capability such as the metals of Group VIII of the Periodic Table, plus chromium, tantalum, tungsten, vanadium, gold and the like which will enhance selectivity to benzene at the higher temperatures of the range contemplated. Preferred metals for this purpose are nickel and cobalt. These metals may be introduced by base exchange or impregnation. In general, the selected metal should be chosen with regard to reaction temperature contemplated. Platinum can be used at high temperatures above about 800° F. which favors dehydrogenation to benzene rings. At lower temperatures, platinum will result in saturation of rings and destruction of product. Nickel can be used effectively at those lower temperatures.

Temperatures for the catalyst used according to this invention may vary depending upon design factors of the equipment. Generally these lie between 550° F. and 1000° F. Pressures will also be dictated, at least in part, by design factors of the equipment and may vary from 100 to 2000 lb. per square inch gauge.

In general, a temperature will be chosen which suits commercial needs at a particular place and time. It is generally true that higher temperatures tend to increase the yield of benzene. Based on this fact, it will be clear that a temperature can be chosen to maximize either benzene or xylenes.

In this connection, it is noted that the temperature of reaction is related to character of the hydrogenation of metal, if any, on the catalyst. Many prior art aromatic processing catalysts employ a metal of the platinum group. These are very potent hydrogenation catalysts. At temperatures much below 800° F., hydrogenation of the ring destroys greater amounts of product, the more the temperature is reduced. At the higher temperature thermodynamic equilibria favor the benzene ring. The present catalysts are effective with such metals as nickel which gave negligible ring hydrogenation at the lower temperatures here possible. In general, it is preferred to use these less potent metal catalysts in this invention to afford temperature flexibility with consequent capability for high throughput.

Suitable space velocities vary from 0.5 to 10 by weight.

The process requires the presence of hydrogen. Preferably, the smallest amount of hydrogen consistent with the desired rate and selectivity of conversion and with adequate catalyst life between regenerations will be selected to minimize the load on compressors, heat exchangers, etc. The hydrogen admixed with charge will generally lie between about 0.5 and 10 mols of hydrogen per mol of hydrocarbon charge.

Severity of the reaction is a function of both temperature and space velocity. Excessive severity will result in undue cracking of the charge. Insufficient severity may permit build up of $C_{10}^+$ aromatics through 9+ disproportionation-type reactions. Thus, the two factors should be adjusted in relationship to each other. For example, space velocity in the lower part of the claimed range will indicate lower temperatures of reaction, and vice versa.

The process above described involves coupling of high temperature isomerization with heavy aromatics processing technology in such a way as to maximize BTX production and to minimize the number of process steps involved. This new process has the following characteristics: Initially, the total reformate product with only a slight reduction in temperature is blended with recycle $C_8$ aromatics and passed through the isomerization reactor. This can be accomplished because, first, benzene and toluene are not converted in that reactor and pass through to the separation plant, and secondly, unlike conventional isomerization, the high temperature type can process paraffins, via hydrocracking to ligher material, without alkylating aromatic rings. This is important since most isomerizer traffic will consist of recycled $C_8$ aromatics. It should be noted that the rate of paraffin cracking decreases with carbon number, thus, the more prevalent $C_6$-paraffins should pass through the isomerizer with only moderate cracking. Since high temperature isomerization (about 870° F. start of cycle) operates at a slightly lower temperature than an aromatic reformer (about 900° F. start of cycle), the temperature adjustment can be made with either a heat exchange system or by direct blending with the $C_8$ recycle steam. In practice, the isomerizer can either be the last reactor of the reformer string, a separate reactor, or part of a "shared" reactor (with heavy aromatics processing). Typically, reformers operate at about 1.5 LHSV, thus sufficient catalyst capacity would be expected in a reforming reactor to accommodate the isomerizer recycle stream which is processed at about 5 to 10 LHSV.

In the isomerizer, the primary reactions will be xylene isomerization, paraffin cracking, and the dealkylation of $C_2^+$ side chains from aromatic rings. Examples of dealkylation are ethylbenzene to benzene, ethylmethylbenzene to toluene, and ethydimethylbenzene to xylene. In a single pass operation it is possible to dealkylate up to 80+% of the ethyl and propyl benzenes, resulting in higher yields of the more commercially valuable BTX from the $C_9^+$ reformate charged. The quantity and composition of BTX produced depends on the composition of the $C_9^+$ reformate charged. However, yields of 0.25 lb. BTX/lb $C_9+$ charged (about 0.7 lb. BTX/lb $C_9+$ reacted) do not seem unreasonable for single pass operation. The preferred catalyst is a Pt-ZSM-5 type with $SiO_2/Al_2O_3 \geq 500$. The isomerizer operates at essentially zero ring loss, thus no aromatic rings are lost in this operation. Following isomerization the product goes with the heavy aromatics processing product to a common separation plant, where the $C_5^-$ material is removed, benzene is recovered, $C_8$ aromatics (after paraxylene removal) are recycled to extinction, and toluene with $C_9^+$ aromatics are sent to heavy aromatics processing. Insofar as paraffins are present in the system, the possibility exists that co-boiling paraffins may contaminate the benzene product. If so, these paraffins can be removed by solvent extraction. It should be noted that if this is necessary, it is a much cheaper operation than to extract paraffins from the total reformate feed. Aside from their presence in the benzene stream, paraffins are not a contaminant, since any paraffins which co-boil with the $C_8$ aromatics stream would pass through the paraxylene crystalizer and return to the isomerizer, while paraffins in the $C_9^+$ stream will not effect performance of heavy aromatics processing.

The primary purpose of heavy aromatics processing is to produce benzene and xylene from the toluene and $C_9^+$ aromatic feed. This is carried out by ring transmethylation with equilibrium around the average methyl group number coupled with a slight methyl group loss and a slight ring loss. The preferred catalyst for this stage is a Ni-ZSM-5 type with $SiO_2/Al_2O_3$ of about 70. The product then goes to the separation plant where benzene and xylene are removed, while toluene and $C_9^+$ aromatics are recycled to extinction in heavy aromatics processing.

There are several advantages to this combined process. Foremost is elimination of the separation plant between the reformer and isomerization. Since it will pass benzene and toluene unreacted and can process paraffins, several distillations and the extraction step are eliminated. Moreover, there is a considerable utility savings in eliminating the related cooldown and heatup. Moreover, since the entire reformate stream is processed through the isomerizer it is possible to use the last reactor in the reformer string as the isomerization reactor.

In terms of application, a significant value of this process is the elimination of the separation steps between the reformer and the xylene isomerization reactor. Thus, it should be noted that this improvement is still applicable if the heavy aromatics reactor is removed from the proposed process stream.

Data are reported below for examples conducted to demonstrate behavior of isomerization according to the present invention. Reference is made to U.S. Pat. No. 3,945,913 and 4,078,990 for data on behavior of the heavy aromatics processing reactor.

Example 1. A charge was prepared to simulate mixture of reformer product with a $C_8$ aromatic recycle stream by blending a cut of reformate boiling above 305° F. with benzene, toluene and mixed $C_8$ aromatics. The catalyst was 30% ZSM-5 (cc Pt) in 70% of alumina binder. The zeolite had a silica/alumina ratio of 1000 and contained 0.4 wt. % platinum. Reaction conditions, composition of the charge and composition of the product are set out in Table 1.

Example 2. Two runs were conducted over a catalyst of 30% ZSM-5 (cc Pt) in alumina. The zeolite had a silica/alumina ratio of 1000 and contained 0.9 wt. % platinum. The charge was prepared by blending 305° F.+ reformate with a mix of eight carbon atom aromatics. See Table 1.

Example 3. A blend of full range reformate with a mixture of eight carbon atom aromatics was processed over the catalyst of Example 1 with results as shown in Table 1.

TABLE I

MANUFACTURE OF BTX FROM REFORMATE PLUS RECYCLE C₈ AROMATICS

| | Example 1 | | Example 2 | | | Example 3 | |
|---|---|---|---|---|---|---|---|
| Temp.(°F.) | | 870 | | 870 | 900 | | 880 |
| PSIG | | 200 | | 200 | 200 | | 200 |
| WHSV | | 8 | | 8 | 4 | | 8 |
| H$_2$/HC | | 5 | | 5 | 5 | | 5 |
| | Charge | | Charge | | | Charge | |
| C$_1$-C$_5$ | | 3.23 | | 2.98 | 4.64 | 1.64 | 5.51 |
| C$_6$ Par | | .36 | | .04 | .06 | 2.56 | 2.08 |
| Benzene | 11.66 | 13.65 | | 3.51 | 6.49 | 0.89 | 4.37 |
| C$_7$ Par | | .05 | | | | 2.44 | .84 |
| Toluene | 13.89 | 15.24 | | 3.11 | 5.50 | 3.18 | 4.12 |
| C$_8$ Par | | .04 | | .01 | .03 | 1.21 | .36 |
| Ethyl Benzene | 7.84 | 5.92 | 11.1 | 7.49 | 3.69 | 12.53 | 7.09 |
| M - XYL | 37.96 | 27.76 | 50.7 | 35.22 | 33.50 | 56.76 | 38.04 |
| P - XYL | 4.71 | 12.10 | 6.5 | 15.25 | 14.90 | 8.36 | 16.94 |
| O - XYL | 5.60 | 10.79 | 6.1 | 13.54 | 14.49 | 6.02 | 16.11 |
| C$_9$+ Par | 2.22 | .40 | 0.7 | .13 | .03 | 0.24 | |
| C$_9$ AR | 5.05 | 6.60 | 15.2 | 11.76 | 10.66 | 3.19 | 2.65 |
| C$_{10}$ AR | 4.50 | 2.71 | 8.4 | 5.56 | 4.58 | 0.88 | 0.75 |
| C$_{11}$ AR | 6.75 | 1.14 | 1.3 | 1.38 | 1.39 | 0.16 | 0.09 |
| Benzene Made | | 1.99 | | 3.51 | 6.49 | | 3.48 |
| Toluene Made | | 1.35 | | 3.42 | 5.50 | | 0.94 |
| Xylene Made | | 2.38 | | 0.71 | −0.41 | | −0.05 |
| % Ring Loss | | −0.50 | | −0.24 | −0.39 | | −2.01 |
| % EB Conv. | | 24.49 | | 32.52 | 66.76 | | 43.41 |
| % C$_9$+ AR Conv. | | 35.88 | | 24.90 | 33.21 | | 16.10 |

We claim:

1. A new use of known apparatus for simultaneously isomerizing xylenes and converting ethylbenzene to products readily separable by distillation from the mixture of C$_8$ aromatics by contacting a mixture of C$_8$ aromatics and hydrogen with a catalyst at conversion conditions of elevated temperature and pressure in a loop comprising an isomerization reactor for the contact aforesaid, distillation means for separating C$_8$ aromatics from lower boiling and higher boiling hydrocarbons, means to transfer hydrocarbon effluent of said isomerization reactor to said distillation means, means for introducing fresh feed C$_8$ aromatics to said loop, a xylene separator for recovery of para xylene, means for transfer of mixed C$_8$ aromatics to said xylene separator, and means to transfer C$_8$ aromatics lean in para xylene from said xylene separator to said isomerization reactor, which new use comprises contacting, in the isomerization reactor of said known apparatus, a vapor phase mixture of hydrogen, said C$_8$ aromatics lean in para xylene and fresh charge material containing alkyl benzenes of more than eight carbon atoms with a zeolite catalyst at a temperature of about 800°–1000° F., a pressure of 150 to 300 pounds per square inch and a weight hourly space velocity between 1 and about 200; said zeolite catalyst having a constraint index of 1 to 12, a silica to alumina ratio greater than 12 and a reduced activity such that less than 2 weight percent of xylene is converted to other compounds when contacted with said catalyst at 900° F., 200 psig and LHSV of 5, mixing said hydrocarbons higher boiling than C$_8$ aromatics with hydrogen, contacting the mixture of hydrogen and said higher boiling hydrocarbons with a porous acidic solid catalyst at a temperature of 550° to 1000° F. and transferring the product of said contacting with a porous acidic solid catalyst to said distillation means.

2. The new use defined by claim 1 wherein said zeolite is in the acid form.

3. The new use defined by claim 1, wherein said silica to alumina ratio is greater than 200.

4. The new use defined by claim 1, wherein said silica to alumina ratio is greater than 500.

5. The new use defined by claim 1 wherein a metal of Group VIII or a compound of such metal is associated with said zeolite.

6. The new use defined by claim 5 wherein said metal is co-crystallized with said zeolite.

7. The new use defined by claim 5 wherein said metal is platinum.

8. The new use defined by claim 1 wherein said zeolite is dispersed in a solid matrix.

9. The new use defined by claim 1 wherein toluene is added to said higher boiling hydrocarbons for contact with said porous acidic solid catalyst.

10. In a process for isomerizing the xylene content of a charge mixture of eight carbon atom aromatic hydrocarbon compounds which mixture contains xylene, and ethylbenzene by contact at conversion conditions with a catalyst comprising a zeolite having a silica/alumina ratio greater than 12 and a constraint index of 1 to 12, the improvement resulting in conversion of ethylbenzene to benzene and conversion of higher alkyl benzenes to benzene, toluene and xylene which comprises including in the charge mixture alkyl aromatics of more than eight carbon atoms maintaining the conversion temperature at about 800° F. to 1000° F., using such catalyst comprising a zeolite of reduced acid activity such that less than 2 weight percent of xylene is converted to compounds other than xylene when contacted with said catalyst at 900° F. 200 psig and LHSV of 5, separating toluene and C$_9$+ aromatics from the products of contact with said zeolite catalyst, reacting said C$_9$+ aromatics in admixture with hydrogen by contacting the same with a porous acidic solid catalyst at a temperature of 550° to 1000° F., and adding the product of said contact with porous acidic solid catalyst to the product of contact with said zeolite catalyst.

11. A process according to claim 10 wherein said zeolite is in the acid form.

12. A process according to claim 10 wherein said zeolite is ZSM-5.

13. A process according to claim 10 wherein said catalyst comprising a zeolite also comprises a metal of Group VIII of the Periodic Table.

14. A process according to claim 13 wherein said zeolite is ZSM-5.

15. A process according to claim 13 wherein said charge mixture is admixed with hydrogen.

16. A process according to claim 15 wherein said zeolite is ZSM-5.

17. A process according to claim 10 resulting in conversion of ethylbenzene to benzene at substantially no loss of xylene in the product as compared to the charge.

18. A process according to claim 10 wherein the said charge mixture contains paraffin hydrocarbons.

19. A process according to claim 10 wherein the said charge mixture consists essentially of aromatic hydrocarbons.

20. A process according to claim 10 wherein said silica/alumina ratio is greater than 200.

21. A process according to claim 10 wherein said silica/alumina ratio is greater than 500.

22. A process according to claim 10 wherein toluene is added to said $C_9^+$ aromatics for contact with said porous acidic solid catalyst.

23. A process for the manufacture of aromatic hydrocarbon which comprises subjecting a hydrocarbon naphtha to catalytic reforming under conditions to convert naphthenes to aromatic hydrocarbons including xylenes, ethylbenzene and alkylbenzenes of more than eight carbon atoms in a reformate reaction product, mixing at least that portion of said reformate boiling above $C_8$ aromatics with a recycle stream hereafter defined which contains xylenes and ethylbenzene, contacting the resultant mixture at 800°–1000° F. with a zeolite catalyst having a constraint index of 1 to 12, a silica/alumina ratio above about 12 and reduced acid activity such that less than 2 weight percent of xylene is converted to compounds other than xylene when contacted with said catalyst at 900° F., 200 psig and LHSV of 5, whereby to isomerize xylene content of said mixture and to convert ethylbenzene and alkylbenzenes of more than eight carbon atoms to benzene, toluene and xylene, distilling the product of said contacting to separate compounds of less than eight carbon atoms and compounds of more than eight carbon atoms from a $C_8$ fraction, recovering at least one xylene isomer from said $C_8$ fraction to provide a stream lean in said recovered isomer and containing xylenes and ethylbenzene, mixing said lean stream with said reformate as the recycle stream aforesaid, reacting said compounds of more than eight carbon atoms in admixture with hydrogen by contacting said admixture with a porous acidic solid catalyst at a temperature of 550° to 1000° F. and adding the product of said contact with porous acidic solid catalyst to the product of contact with said zeolite catalyst.

24. A process according to claim 23 wherein said zeolite is ZSM-5.

25. A process according to claim 23 wherein said zeolite is in the acid form.

26. A process according to claim 23 wherein said contacting with zeolite catalyst is conducted under hydrogen pressure.

27. A process according to claim 23 wherein said zeolite is associated with a metal of Group VIII.

28. A process according to claim 27 wherein said metal is a noble metal of Group VIII.

29. A process according to claim 23 wherein said reformate is treated with a solvent to separate paraffins therefrom.

30. A process according to claim 23 wherein said reformate contains paraffin hydrocarbons.

31. A process according to claim 23 wherein said silica/alumina ratio is greater than 200.

32. A process according to claim 31 wherein said silica/alumina ratio is greater than 500.

33. A process according to claim 27 wherein said metal is co-crystallized with said zeolite.

34. A process according to claim 23 wherein toluene is added to said compounds of more than eight carbon atoms for contact with said porous acidic solid catalyst.

35. In a process for manufacture of at least one of benzene, toluene and xylene from a hydrocarbon naphtha containing carbocyclic single ring components by catalytic reforming of the naphtha under conditions to dehydrogenate carbocyclic rings with production of a reformed naphtha containing benzene, toluene, xylenes, ethylbenzenes and alkylbenzenes of more than eight carbon atoms and thereafter separating benzene, toluene or xylene from the reformed naphtha, the improvement which comprises contacting said reformed naphtha or a fraction thereof containing alkylbenzenes of more than eight carbon atoms and hydrogen at 800°–1000° F. with a zeolite catalyst having a constraint index of 1 to 12, a silica/alumina ratio above about 12 and reduced acid activity such that less than 2 weight percent of xylene is converted to compounds other than xylene when contacted with said catalyst at 900° F., 200 psig and LHSV of 5, whereby to convert ethylbenzene and alkylbenzenes of more than eight carbon atoms to benzene, toluene and xylene, and recovering at least one of benzene, toluene or xylene as a product.

36. A process according to claim 35 wherein said catalytic reforming is conducted in the presence of hydrogen and the entire effluent of said catalytic reforming is contacted with said zeolite catalyst.

37. A process according to claim 35 wherein xylenes are added to the reformed naphtha or fraction thereof for contact with said zeolite catalyst.

* * * * *

UNITED STATES PATENT AND TRADEMARK OFFICE
CERTIFICATE OF CORRECTION

PATENT NO. : 4,211,886
DATED : July 8, 1980
INVENTOR(S) : Samuel A. Tabak and Roger A. Morrison It is certified that error appears in the above-identified patent and that said Letters Patent are hereby corrected as shown below:

Column 2, line 39, "$C_9'$" should be --$C_9^+$--.

Column 3, line 55, "remore" should be --remove--.

Column 6, line 1, "constraing" should be --constraint--.

Column 4, line 58, "2" should be --5--.

Column 13, line 12, "9+" should be --$C_9^+$--.

Column 13, line 64, "$\geqq 500$" should be --$\geq 500$--.

Signed and Sealed this

Second Day of December 1980

[SEAL]

Attest:

SIDNEY A. DIAMOND

Attesting Officer

Commissioner of Patents and Trademarks